US012130087B2

(12) United States Patent
Whitely (10) Patent No.: US 12,130,087 B2
(45) Date of Patent: Oct. 29, 2024

(54) HEAT PACK WITH SUPERCOOLED AQUEOUS SALT SOLUTION AND GLYCERIN

(71) Applicant: RAPID AID CORP., Mississauga (CA)

(72) Inventor: Jeffrey Thomas Whitely, Millgrove (CA)

(73) Assignee: RAPID AID CORP., Mississauga (CA)

( * ) Notice: Subject to any disclaimer, the term of this patent is extended or adjusted under 35 U.S.C. 154(b) by 417 days.

(21) Appl. No.: 17/521,802

(22) Filed: Nov. 8, 2021

(65) Prior Publication Data

US 2022/0146211 A1     May 12, 2022

Related U.S. Application Data (60) Provisional application No. 63/111,183, filed on Nov. 9, 2020.

(51) Int. Cl.
    *F28D 20/02*       (2006.01)
    *A61B 5/15*        (2006.01)
    (Continued)

(52) U.S. Cl.
CPC ...... *F28D 20/021* (2013.01); *A61B 5/150022* (2013.01); *A61B 5/150122* (2013.01);
(Continued)

(58) Field of Classification Search
CPC . F24V 30/00; F24D 20/021; A61B 5/150022; A61B 5/150122; A61B 5/150076; A61B 2503/04; A61F 7/03; A61F 7/106; A61F 7/00; A61F 7/0085; A61F 2007/0215; A61F 2007/022; A61F 2007/0225; A61F 2007/0276;
(Continued)

(56) References Cited

U.S. PATENT DOCUMENTS

| 3,951,127 A * | 4/1976 | Watson | F28D 20/028 |
| | | | 607/114 |
| 4,205,685 A * | 6/1980 | Yoshida | A61K 9/70 |
| | | | 607/96 |

(Continued)

FOREIGN PATENT DOCUMENTS

| CA | 1119404 A | 3/1982 |
| CA | 2305093 A1 | 10/2000 |

(Continued)

OTHER PUBLICATIONS

Heat in a Click Ireland, "Frequently Asked Questions." Heat in a Click, Ltd., Mar. 8, 2013, URL: https://heatinaclick.ie/faq/. Retrieved from the Internet on May 1, 2020.

(Continued)

*Primary Examiner* — Ko-Wei Lin
(74) *Attorney, Agent, or Firm* — Perry + Currier Inc.

(57) ABSTRACT

A heat pack using supercooled aqueous salt solution that resists premature activation at low temperatures is disclosed. The heat pack comprises two sheets that are bonded together to form a laminated sheet. The heat pack has a first and second compartment. A frangible seal separates the two compartments. One of the compartments contains a supercooled aqueous salt solution. The salt solution contains 15 to 25 percent glycerin by mass.

16 Claims, 4 Drawing Sheets

(51) Int. Cl.
*A61F 7/03* (2006.01)
*F24V 30/00* (2018.01)

(52) U.S. Cl.
CPC ............... *A61F 7/03* (2013.01); *F24V 30/00* (2018.05); *A61B 2503/04* (2013.01)

(58) Field of Classification Search
CPC ...... A61F 2007/0293; A61F 2007/0089; A61F 2007/0098; Y02E 60/14
See application file for complete search history.

(56) References Cited

U.S. PATENT DOCUMENTS

| | | | |
|---|---|---|---|
| 4,451,383 A | | 5/1984 | Arrhenius |
| 5,723,063 A | | 3/1998 | Jie |
| 6,099,556 A | * | 8/2000 | Usui ..................... F24V 30/00 |
| | | | 126/263.01 |
| 6,318,359 B1 | * | 11/2001 | Schmidt .................. A61F 7/03 |
| | | | 126/263.03 |
| 6,537,309 B2 | | 3/2003 | Sharma et al. |
| D804,046 S | * | 11/2017 | Whitely ..................... D24/207 |
| 2009/0293859 A1 | * | 12/2009 | Coffey .................. F24V 30/00 |
| | | | 126/263.01 |
| 2014/0109890 A1 | * | 4/2014 | Pedicini .................. B23P 19/00 |
| | | | 126/263.02 |
| 2015/0173942 A1 | * | 6/2015 | Whitely .................... A61F 7/02 |
| | | | 607/114 |
| 2020/0138625 A1 | * | 5/2020 | Hope ...................... A61F 7/034 |
| 2021/0261843 A1 | * | 8/2021 | Kawakami ................ C08J 5/18 |
| 2021/0293489 A1 | * | 9/2021 | Mitsui ........................ C08J 5/18 |
| 2021/0340423 A1 | * | 11/2021 | Li .......................... C09K 5/063 |

FOREIGN PATENT DOCUMENTS

| | | | |
|---|---|---|---|
| CN | 102755664 A | 10/2012 | |
| CN | 204033580 U | 12/2014 | |
| CN | 110819309 A | 2/2020 | |
| EP | 2883928 B1 | 4/2019 | |
| EP | 2853576 B1 | 7/2019 | |
| JP | 2013075024 A | * | 4/2013 |

OTHER PUBLICATIONS

PCT/IB2021/060330, Heat Packed With Supercooled Aqueous Salt Solution and Glycerin, Nov. 8, 2021.

* cited by examiner

HEAT PACK WITH SUPERCOOLED AQUEOUS SALT SOLUTION AND GLYCERIN

FIELD

The present invention is directed to disposable heat packs for therapeutic use and more particularly to heat packs employing supercooled aqueous salt solution.

BACKGROUND

Disposable heat packs using supercooled aqueous salt solutions are well-known. These packs typically employ a flexible plastic container which houses the salt solution. The solution is supercooled, meaning it is prepared in a very pure state and then heated to a high temperature. It is then cooled gradually to a temperature below its normal crystallization temperature. When the pack is to be used, crystallization in the solution can be initiated by exposing the solution to air. The latent heat of crystallization warms the pack as the solution turns from liquid to solid phase. If the correct formulation of salt solution is chosen, the phase change occurs at a constant temperature in a narrow range which is appropriate to warm human skin, The reaction is predictable and stable and lasts several minutes—enough for the pack to perform its task.

There are a few methods of packaging the salt solution in order to inject air when triggered by a user. For instance, U.S. Pat. No. 6,318,359 B1, which is incorporated herein by reference, discloses a heat pack with a rupturable seal separating a compartment holding a salt solution from a second compartment holding air.

One issue with this type of heat pack is premature activation. If a single-use heat pack is activated before it reaches the end user, it cannot be used for its intended purpose. In any one shipment of heat packs, some may be unusable. For this reason, heat packs using supercooled salt solutions are somewhat unreliable. Premature activation also contributes to wasted product and decreased revenue.

It was thought that prematurely activated packs were the result of a rupture or leak in the seal that separates the air from the aqueous salt solution. However, premature activation has been observed in packs that present no damage to their rupturable seals. It was not known why some heat packs survived shipment while others were prematurely activated.

Eventually, it was found that low temperatures can cause the heat packs to self-activate. It was observed that heat packs arranged in the outer layer of a shipping container were more likely to be prematurely activated when delivered to the end user as compared to the heat packs from a center layer. Furthermore, a greater percentage of heat packs were found to be prematurely activated during colder winters.

Normally, the aqueous salt solution is prepared such that the supercooled solution remains stable at ambient temperatures found in homes, hospitals and their related storage areas. However, during the manufacturing and distribution process, heat packs may experience temperatures that are lower than room temperature. Under these conditions, the salt solution may be prematurely activated.

Although it is possible to ship heat packs in heated vehicles and shipping containers, this solution is both costly and error prone. Heat packs stowed in the outer layers of a heated truck may nonetheless experience low temperatures. Further, some heat packs may be preactivated during at transfer points within the delivery chain. Premature activation is particularly common during colder winters and on particularly cold days. The issue is further complicated by the number of entities involved in the distribution process; supply chains are often too complex to reasonably control the entire journey.

Some heat packs containing supercooled aqueous salt solutions are known to include organic compounds, however these heat packs disclose concentrations of organic compounds between 1 and 10% by mass. European Patent No. 2,853,576 B1 describes a heat pack containing a supercooled aqueous solution comprising 1-9% glycerin. However, testing results disclosed in that document appear to suggest that resistance to pre-activation is reduced when glycerin exceeds 2% of the total solution. In Example J1, a composition comprising 2% glycerin by weight was preserved in a supercooled state at −20° C. for between 3 to 5 hours. In comparison, solutions containing higher concentrations of glycerin resisted pre-activation for shorter periods of time. In Example J5, a solution containing 9% glycerin by weight was preserved at −20° C. for 2 to 3 hours, and in Example J9, a composition comprising 6% glycerin by weight was preserved at −20° C. for just 1 to 2 hours.

The prior art suggests that an ideal concentration of glycerin for preserving a supercooled state is around 2% and that increasing the glycerin concentration above 2% will make a supercooled aqueous salt solution more susceptible to pre-activation.

Additionally, organic compounds are thought to reduce the rate of crystallization of a supercooled salt solution, thereby decreasing the heat released on activation. Since heat packs for medical or therapeutic purposes must reach a prescribed maximum temperature ($T_{max}$), organic compounds may not be suitable as anti-freezing agents.

SUMMARY

It is an aspect of the present invention to provide a heat pack using supercooled aqueous salt solution that resists premature activation.

The above aspects can be attained by a heat pack comprising a container that has two layers of flexible sheet material that are bonded together to form laminated sheet material. The container has a first and second compartment. A rupturable seal separates the two compartments. One of the compartments contains air and the other compartment houses a supercooled aqueous salt solution. The salt solution contains 15 to 25 percent glycerin by mass.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION

The present invention is described with respect to a heat pack with a supercooled aqueous salt solution that resists premature activation.

"Glycerol" and "glycerin" and "glycerine" are herein used interchangeably to refer to the same polyol compound having the simple formula $C_3H_8O_3$.

"Salt" herein refers to any chemical compound consisting of cations and anions.

"Aqueous salt solution" herein refers to a solution comprising water as the solvent and at least one salt as a solute. "Salt solution" is used interchangeably with "aqueous salt solution".

"Supercooled" herein refers to a liquid or gas that has been cooled below its freezing point without becoming a solid.

"By mass" herein refers to a method of indicating the relative compositions of a component (or components) in a solution. When the composition of a component(s) is indicated as a percentage "by mass", the mass of the component(s) is measured as a percentage of the total mass of the solution.

"Frangible" herein refers to something that is readily broken.

"Seal" herein refers to a closure that blocks the passage of liquids.

"Latent heat of fusion" or "enthalpy of fusion" are herein used interchangeably to refer to the energy that is released when a supercooled liquid changes from liquid to solid.

$T_{max}$ or "maximum temperature" herein refers to greatest temperature reached by a heat pack after it is activated. The $T_{max}$ for a particular solution is determined by the latent heat of fusion.

"Sodium acetate" herein refers to sodium acetate trihydrate.

It was thought that prematurely activated packs were the result of a rupture or leak in the seal that separates the air from the aqueous salt solution. However, premature activation has been observed in packs that present no damage to their rupturable seals. It was not known why some heat packs survived shipment while others were prematurely activated.

Eventually, it was found that low temperatures can cause the heat packs to self-activate. It was observed that heat packs arranged in the outer layer of a shipping container were more likely to be prematurely activated when delivered to the end user as compared to the heat packs from a center layer. Furthermore, a greater percentage of heat packs were found to be prematurely activated during colder winters.

Normally, the aqueous salt solution is prepared such that the supercooled solution remains stable at ambient temperatures found in homes, hospitals and their related storage areas. However, during the manufacturing and distribution process, heat packs may experience temperatures that are lower than room temperature. Under these conditions, the salt solution may be prematurely activated.

Although it is possible to ship heat packs in heated vehicles and shipping containers, this solution is both costly and error prone. Heat packs stowed in the outer layers of a heated truck may nonetheless experience low temperatures. Further, some heat packs may be preactivated during at transfer points within the delivery chain. Premature activation is particularly common during colder winters and on particularly cold days. The issue is further complicated by the number of entities involved in the distribution process; supply chains are often too complex to reasonably control the entire journey.

Some heat packs containing supercooled aqueous salt solutions are known to include organic compounds, however these heat packs disclose concentrations of organic compounds between 1 and 10% by mass. European Patent No. 2,853,576 B1 describes a heat pack containing a supercooled aqueous solution comprising 1-9% glycerin. However, testing results disclosed in that document appear to suggest that resistance to pre-activation is reduced when glycerin exceeds 2% of the total solution. In Example J1, a composition comprising 2% glycerin by weight was preserved in a supercooled state at −20° C. for between 3 to 5 hours. In comparison, solutions containing higher concentrations of glycerin resisted pre-activation for shorter periods of time. In Example J5, a solution containing 9% glycerin by weight was preserved at −20° C. for 2 to 3 hours, and in Example J9, a composition comprising 6% glycerin by weight was preserved at −20° C. for just 1 to 2 hours.

The prior art suggests that an ideal concentration of glycerin for preserving a supercooled state is around 2% and that increasing the glycerin concentration above 2% will make a supercooled aqueous salt solution more susceptible to pre-activation.

Additionally, organic compounds are thought to reduce the rate of crystallization of a supercooled salt solution, thereby decreasing the heat released on activation. Since heat packs for medical or therapeutic purposes must reach a prescribed maximum temperature ($T_{max}$), organic compounds may not be suitable as anti-freezing agents.

A heat pack comprising a container that has two layers of flexible sheet material that are bonded together to form laminated sheet material is disclosed. The container has a first and second compartment. A rupturable seal separates the two compartments. One of the compartments contains air and the other compartment houses a supercooled aqueous salt solution. The salt solution contains 15 to 25 percent glycerin by mass.

A number of salts are suitable for preparing the aqueous salt solution including sodium thiosulphate (Sigma Aldrich, Oakville, Canada) and sodium acetate trihydrate (Sigma Aldrich, Oakville, Canada). An effective aqueous salt solution for use in the heat pack has been found to be an aqueous solution of sodium acetate trihydrate. While solution strength can range, a mixture of 100 grams water and approximately 50 to 100 grams sodium acetate trihydrate has proven effective. The solution may be heated to between 77 to 88 degrees Celsius (170 to 190 degrees Fahrenheit) and then super-cooled. The solution may then be placed in a heat pack.

Solutions in the ranges indicated have been found desirable as they can be easily triggered to provide heat having a substantially constant temperature. If the super-cooled solution has been heated to a high enough temperature above its melting point before being cooled, it will also remain stable in its super-cooled state even when cooled to temperatures below its melting point. The super-cooled solution will maintain this state until triggered by mixture the contents of the second compartment.

Use of sodium acetate trihydrate in solution is one chemical that has proven effective. Other chemicals however with suitable characteristics could be used. One aspect that is required is a stable and relatively rapid phase change once crystallization initiates. A number of applications require that the temperature of the phase change suit warming of human skin.

The latent heat of fusion the solution used in one embodiment reliably heats a heat pack to within a narrow range of about 38.3 to 40 degrees Celsius (101 to 104 degrees Fahrenheit), most often near 40 degrees Celsius (104 degrees Fahrenheit). In another embodiment, the latent heat of fusion of the solution heats a heat pack to within a narrow range of about 41.7-43.3 degrees Celsius (107 to 110 degrees Fahrenheit). The phase change, and thus heating, occurs in a few seconds, and the heat is retained for several minutes. With gentle kneading the heat distributes evenly.

Adding glycerin to the aqueous salt solution may prevent premature activation, particularly at temperatures below −10° C. The concentration of glycerin in the solution may range, depending on the desired amount of heat to be released by the activated solution and the desired stability of the solution. A solution comprising approximately 15 to 25 percent glycerin by mass has proven effective.

Some embodiments of the heat pack may be used to warm the heel of an infant for blood collection. Applying heat to the heel of an infant increase capillary blood flow in the infant's foot which facilitates blood collection. Accordingly, the composition of the aqueous salt solution may be selected to achieve a latent heat of fusion that is suitable for infant heel warming. In one example, the solution may comprise glycerin (22%±0.5), water (33.5%±0.5), and sodium acetate (44.5%±0.5) by mass. This solution may remain stable at −30° C. In some instances, it may remain stable at temperatures below −30° C. When activated, the solution may reach a maximum temperature of 38.3-40° C. (101-104° F.).

Other embodiments of the heat pack may be used for therapeutic purposes. Accordingly, the composition of the aqueous salt solution may be selected to achieve a latent heat of fusion that is suitable for therapeutic purposes. In one example, the solution may comprise glycerin (19.1%±0.5), water (34.1%±0.5), and sodium acetate (46.9%±0.5) by mass. This solution may remain stable at −30° C. In some instances, it may remain stable at temperatures below −30° C. When activated, the solution may reach a maximum temperature of 41.7-43.3° C. (107-110° F.).

As stated, other chemicals with different properties and particular different temperatures of phase change may also be used. For certain applications much higher temperatures might be desirable which would require the use of chemicals having higher heats of latent fusion. Heat packs generally could be used for heating a number of things in addition to humans, including other liquids, foods, etc. Some of these applications could require that the heat pack develop temperatures of 54 to 66 degrees Celsius (130 to 150 degrees Fahrenheit) or higher.

1.1 Freezing Point of Glycerin Dilutions

A study was conducted to evaluate the effect of water dilution on the freezing and boiling point of glycerin. The results are shown in Table 1 below.

For compositions between 66.7 and 100% glycerin, the freezing point decreases as the ratio of glycerin to water decreases. However. For compositions below 66.7% glycerin, the freezing point increases as the ratio of glycerin to water decreases. These test results show that a glycerin to water ratio of 2:5 has a freezing temperature of −15.6° C.

TABLE 1

| Concentration Glycerin (% by mass, weight) | Specific Gravity (at 60° F., 15.6° C.) | Freezing Point ° F. | Freezing Point ° C. | Boiling Point ° F. | Boiling Point ° C. |
| --- | --- | --- | --- | --- | --- |
| 98.2 | 1.261 | 56 | 13.3 | 554 | 290 |
| 95 | 1.253 | 46 | 7.8 | 332 | 167 |
| 90 | 1.24 | 29 | −1.7 | 281 | 138 |
| 80 | 1.213 | −5 | −20.6 | 250 | 121 |
| 70 | 1.185 | −38 | −38.9 | 237 | 114 |
| 66.7 | 1.178 | −51 | −46.1 | 234 | 112 |
| 60 | 1.157 | −30 | −34.4 | 228 | 109 |
| 50 | 1.129 | −9 | −22.8 | 223 | 106 |
| 40 | 1.102 | 4 | −15.6 | 219 | 104 |
| 30 | 1.075 | 15 | −9.4 | 217 | 103 |
| 20 | n/a | 23 | −5 | n/a | n/a |
| 10 | n/a | 28.9 | −1.7 | n/a | n/a |

1.2 Pre-Activation Testing

A study was conducted on supercooled sodium acetate solution and variable compositions of glycerin. Each sample was contained in a separate water bag composed or polyethylene or polyethylene terephthalate. Testing was conduct on 5 water bags containing 0% glycerin, 5 water bags containing 5% glycerin, 5 water bags containing 12% glycerin, 5 water bags containing 20% glycerin, and 5 water bags containing 23% glycerin. Sodium acetate comprised 44.5% of each solution by weight and the balance of the weight was water. The total mass of solution in each water bag was 232±12 grams.

First, the samples were placed in a room with a temperature 21-24.5° C. (70-76° F.) until all samples reached room temperature. Next, the samples were placed in a high-low temperature test chamber (LNEYA; Wuxi, Jiangsu) at the same time. The temperature in the test chamber was reduced to −10° C. (14° F.) in four hours, and the samples were observed for pre-activation. The temperature was further reduced from −10° C. (14° F.) to −15° C. (5° F.) in four hours, and the samples were observed for pre-activation. The temperature was further reduced from −15° C. (5° F.) in to −20° C. (−4° F.) in four hours, and the samples were observed for pre-activation. The temperature was further reduced from −20° C. (−4° F.) to −25° C. (−13° F.) in four hours, and the samples were observed for pre-activation. The temperature was further reduced from −25° C. (−13° F.) to −30° C. (−22° F.) in four hours, and the samples were observed for pre-activation.

The test results are summarized in Table 2, below. The checkmarks indicate the temperature at which the pre-activation was first observed in the respective test item.

TABLE 2

| | | Test Item: | | | | | | | | | | | | | | | | | | | | |
|---|---|---|---|---|---|---|---|---|---|---|---|---|---|---|---|---|---|---|---|---|---|---|
| | | 0% glycerin | | | | | 5% glycerin | | | | | 12% glycerin | | | | | 20% glycerin | | | | | 23% glycerin | |
| | | 1 | 2 | 3 | 4 | 5 | 1 | 2 | 3 | 4 | 5 | 1 | 2 | 3 | 4 | 5 | 1 | 2 | 3 | 4 | 5 | 1 | 2 | 3 | 4 | 5 |
| Temperature for pre-activation | −10° C. | | | | | | | | | | | | | | | | | | | | | | | | | |
| | −15° C. | ✓ | | | | | | | | | ✓ | | | | | | | | | | | | | | | |
| | −20° C. | / | ✓ | ✓ | ✓ | ✓ | / | ✓ | ✓ | ✓ | ✓ | | | | | | | | | | | | | | | |
| | −25° C. | / | / | / | / | / | / | / | / | / | / | ✓ | ✓ | ✓ | ✓ | ✓ | | | | | | | | | | |
| | −30° C. | / | / | / | / | / | / | / | / | / | / | / | / | / | / | / | ✓ | ✓ | | | | | | | | |

Freezing does not occur in temperatures between room temperature and −10° C. (14° F.). Solutions comprising 0% or 5% glycerin began freezing at temperatures between −10° C. (14° F.) and −20° C. (−4° F.). Solutions comprising 12% glycerin froze at temperatures between −20° C. (−4° F.) and −25° C. (−13° F.). Solutions comprising 20% glycerin began freezing at temperatures below −25° C. (−13° F.). Solutions comprising 23% glycerin did not freeze at −30° C. (−22° F.). It was concluded that pre-activation of supercooled aqueous salt solutions is related to temperature and the proportion of glycerin.

1.3 Long Term Freezing Test

For this study, heat packs containing supercooled aqueous salt solution were tested for long-term resistance to freezing. Heat packs were packaged according to the methods described later with respect to FIGS. 1-4. 162 heat packs were packaged, each containing one of the four following compositions:

A. Glycerin (19.1%±0.5), water (34.1%±0.5), sodium acetate (46.9%±0.5) by mass
B. Water (53.1%±0.5), sodium acetate (46.9%)
C. Glycerin (22%±0.5), water (33.5%±0.5), sodium acetate (44.5%±0.5) by mass.
D. Water (55.5%±0.5), sodium acetate (44.5%±0.5)

The heat packs were stored in a freezer at −17° C. (1.4° F.) for 6 consecutive days. Pre-activated heat packs were counted and removed. Then, the heat packs were stored in the freezer at −27° C. (−16.6° F.) for 3 consecutive days. Again, the pre-activated heat packs were counted and removed. The test results are shown below in Table 3.

TABLE 3

| Composition | A | B | C | D |
|---|---|---|---|---|
| Units Tested | 21 units | 21 units | 95 units (4 inner cases) | 25 units (1 inner case) |
| Number of pre-activated units when samples stored @−17° C. for 6 days | 0 unit (0%) | 21 units (100%) | 1 units (1%) | 1 unit (4%) |
| Number of pre-activated units when samples stored @−27° C. for 3 days | 3 units (14%) | N/A (100%) | 4 units (4.2%) | 6-units (24%) |

The testing shows that adding glycerin to a heat pack formulation reduces the freezing point of the solution. Reducing the freezing point significantly reduces the pre-activation of the supercooled salt solution when samples are stored at extremely low temperatures for extended periods of time.

1.4 Maximum Temperature Testing

Another study was conducted to understand the effect of glycerin on the maximum temperature ($T_{max}$) of the heat pack. A number of heat packs were prepared according to the methods described later with respect to FIGS. 1-4. Three samples with each of the following compositions were tested:

Composition A: Glycerin (19.1%±0.5), water (34.1%±0.5), and sodium acetate (46.9%±0.5) by mass
Composition C: Glycerin (22%±0.5), water (33.5%±0.5), and sodium acetate (44.5%±0.5) by mass.

Each sample was activated by rupturing the frangible seal. Then, the temperature of each sample was measured every minute for 45 minutes, using a resistance temperature detector (RTD) temperature recorder (Omega, Norwalk, United States). The results are summarized in Table 2, below.

TABLE 4

| Compo- | $T_{max}$ | | |
|---|---|---|---|
| sition | Sample 1 | Sample 2 | Sample 3 (F) |
| A | 42.7° C. (108.9° F.) | 42.4° C. (108.3° F.) | 41.9° C. (107.4° F.) |
| C | 39° C. (102.2° F.) | 38.9° C. (102.0° F.) | 38.9° C. (102.1° F.) |

Further maximum temperature tests were conducted on heat packs containing compositions E and F.

Composition E: Glycerin (22.0%), water (33.5%), and sodium acetate (44.5%) by mass
Composition F: Glycerin (19.1%), water (34.1%), and sodium acetate (46.9%) by mass.

In one test, $T_{max}$ for a sample containing Composition E was found to be 39.48° C. (103.064° F.). The results for 8 samples containing Composition F are summarized in Table 5, below.

TABLE 5

| Sample Number | Maximum Temperature Reached |
|---|---|
| 1 | 42.63° C. (108.734° F.) |
| 2 | 43.02° C. (109.436° F.) |
| 3 | 43.3° C. (109.94° F.) |
| 4 | 41.83° C. (107.294° F.) |
| 5 | 42.45° C. (108.41° F.) |
| 6 | 39.48° C. (103.064° F.) |
| 7 | 43.18° C. (109.724° F.) |
| 8 | 42.42° C. (108.356° F.) |

The tests show that heat packs containing the supercooled aqueous salt solutions described above have $T_{max}$ values in a range suitable for infant heel warmers and therapeutic warm packs. An ideal $T_{max}$ for infant heel warmers may be 38-40° C. (101-104° F.). The $T_{max}$ tested for compositions C and E falls within this range. An ideal $T_{max}$ for therapeutic warm packs may be 41.7-43.3° C. (107-110° F.). As shown in Tables 4 and 5 above, the $T_{max}$ tested for compositions A and F falls within this range.

2.1 Heat Pack

Figure 1:
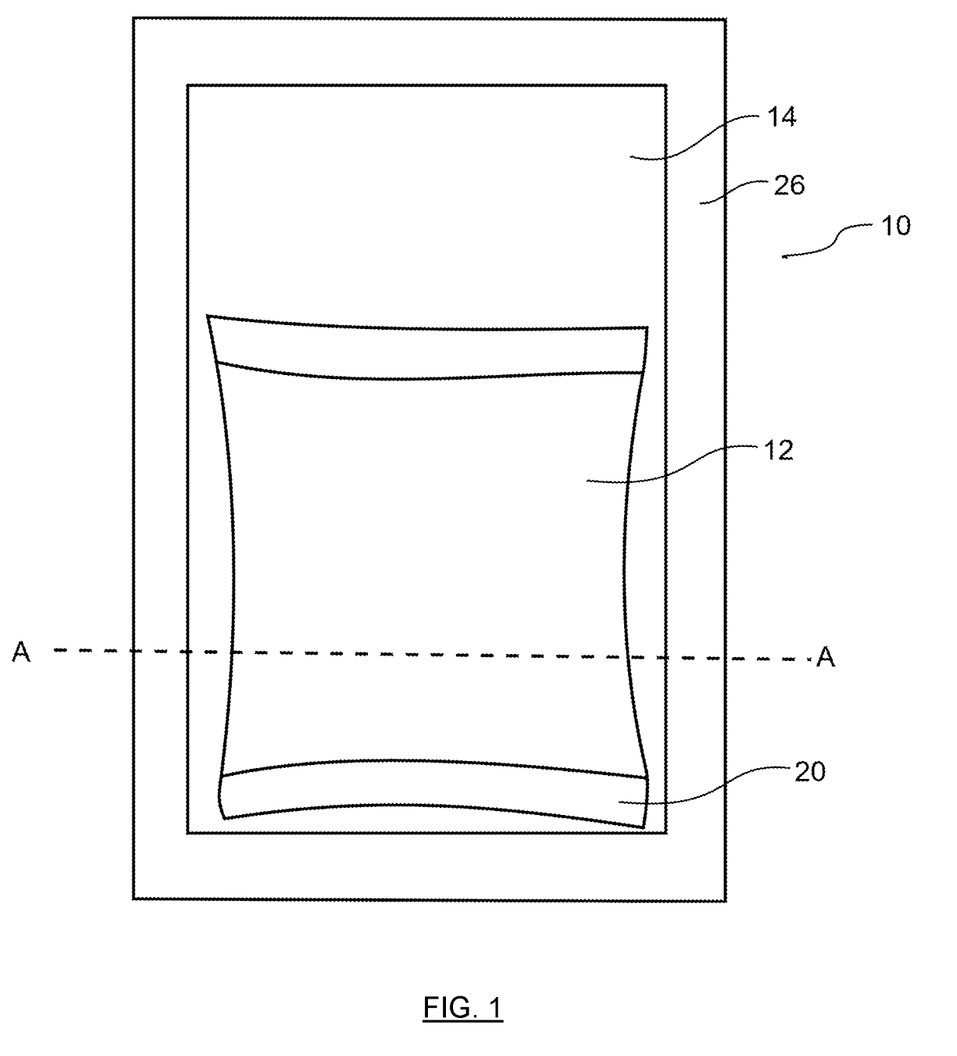
FIG. 1 is a top view of one embodiment showing a salt solution in a first compartment
Figure 2:
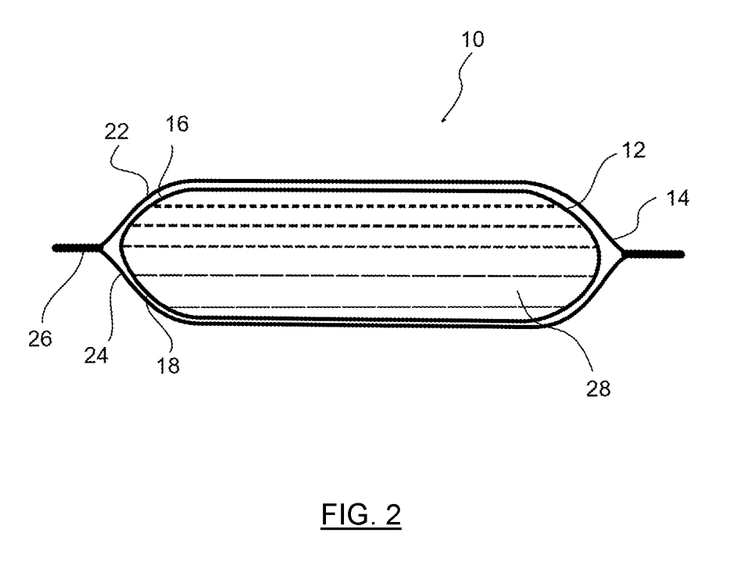
FIG. 2 is a section view along line A of FIG. 1.

Referring now to FIGS. 1 and 2, a heat pack 10 having a first compartment 12 and a second compartment 14 is illustrated. In this embodiment, the heat pack 10 comprises four sheets 16, 18, 22, 24, but the heat pack 10 may comprise any suitable number of sheets above one. The sheets 16, 18, 22, 24 are bonded together to form a laminated sheet having an interior space. The heat pack 10 further comprises a frangible seal which separates the first compartment 12 from the second compartment 14.

The sheets 16, 18, 22, 24 may be configured to form the first compartment 12 and the second compartment 14. A number of configurations may be suitable for forming the first and second compartment. One possible configuration is illustrated in FIGS. 1-4. The first sheet 22 and the second sheet 24 may be bonded together along their peripheral edges 26 to form the second compartment 14. The third sheet 16 and the fourth sheet 18 may be bonded along their peripheral edges 20 to form the first compartment 12. The third and fourth sheets 16, 18 may be contained within the second compartment. The third and fourth sheets 16, 18 may be bonded to the first and second sheets 12, 14 or they may be detached from the first and second sheets 12, 14. In this embodiment, The first compartment 12 is the same shape as the second compartment 14 but the first compartment 12 is smaller thus fitting inside the second compartment 14. In this embodiment, one or both of the third sheet 22 and the fourth sheet 24 may comprise the frangible seal. The frangible seal may be a weak point or seam in the third and/or fourth sheet 22, 24.

In another possible configuration (not shown), the first sheet and the second sheet may be bonded together along their peripheral edges to form an interior space. The interior space may be divided into the first and second compartments. The interior space could be divided with a third sheet or with a seam between the first and second sheets 16, 18. If the interior space is divided with a third sheet, the third sheet may comprise the frangible seal which could be a weakened point or seam. If the interior space is divided with a seam, the seam may comprise the frangible seal.

In the embodiments shown, the sheets 16, 18, 22, 24 are generally rectangular in shape and each pair of sheets is approximately the same size and configuration, however the sheets are not particularly limited.

The sheets 16, 18, 22, 24 may comprise a flexible or semi-flexible material. To facilitate fabrication of the heat pack 10, the sheets may be heat sealable. Many suitable materials exist including polyesters and polynylons. One particularly suitable heat sealable plastic material is polyethylene. Polyethylene is low to medium density, is not expensive, and is easily heat sealed over a wide temperature range. Polyethylene sheet material is very flexible and will readily elongate when placed in tension. In certain applications, the use of a poly-based laminate film has also been successful. For example, the third and fourth sheets can be made from a laminate while the first and second sheets may be made from a standard polyethylene material.

The bonding between the first and second sheets and the third and fourth sheets may create a hermetic seal.

Figure 3:
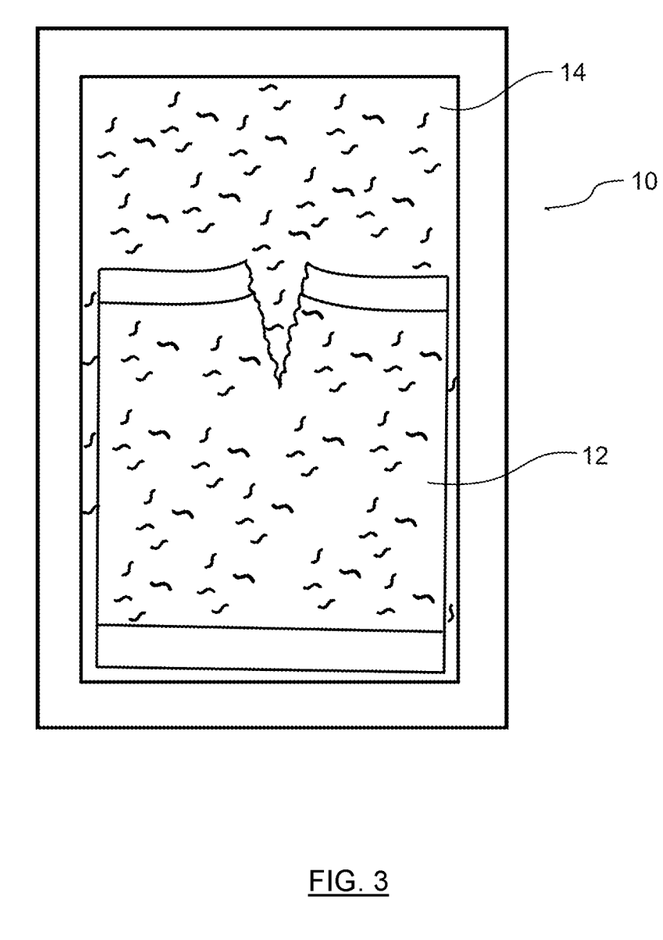
FIG. 3 is a top view of the embodiment of FIG. 1 showing the pack after activation.

Both the first and second compartments 12 and 14 may be adapted to contain a supercooled aqueous salt solution 28 prepared according to the method described above. In the present embodiment, the supercooled aqueous salt solution is contained in the first compartment 12, but in other embodiments, the second compartment may contain the supercooled aqueous salt solution 28. Whichever compartment does not contain the supercooled aqueous salt solution 28 may be adapted to trigger the supercooled aqueous salt solution to freeze when the frangible seal is broken, as shown in FIG. 3. The compartment may contain, but is not limited to: nothing, a gas, metal, or atmospheric air.

To trigger the pack the user applies firm but reasonable pressure in a squeezing motion to the exterior of the pack. As solution 28 is generally an incompressible liquid such as water, the resultant force tends to force the solution out of the first compartment 12 by rupturing one or more of the seams on the edges of the first compartment 20, thereby allowing the solution 28 and the air from the second compartment 14 to mix. This is sufficient to reliably trigger the crystallization of the super-cooled solution, thereby releasing the latent heat of fusion. The heat pack 10 is thus warmed and can be applied to the user. The rupturing of the first compartment 12 is shown in FIG. 3.

The sheet can be chosen and manipulated so that the force required to rupture the frangible seal can be easily achieved with one hand. Due to the fluid nature of the pack however, it is highly improbable that any force accidentally applied would trigger the heat pack. For example, handling during storage and transport are unlikely to activate the heat pack. If desired the first compartment 12 may further be secured to the second compartment 14 at one seam by heat sealing all four sheets together for a distance along one edge. This may facilitate optimal force distribution when the pack is squeezed externally allowing the rupture to occur in the most efficient manner.

If greater consistency is desired in the crystallized solution, say for larger packs, a viscosity enhancing agent or gelling agent may be added to the solution. One such agent that has proven effective is hydroxy ethyl cellulose polymer.

Figure 4:
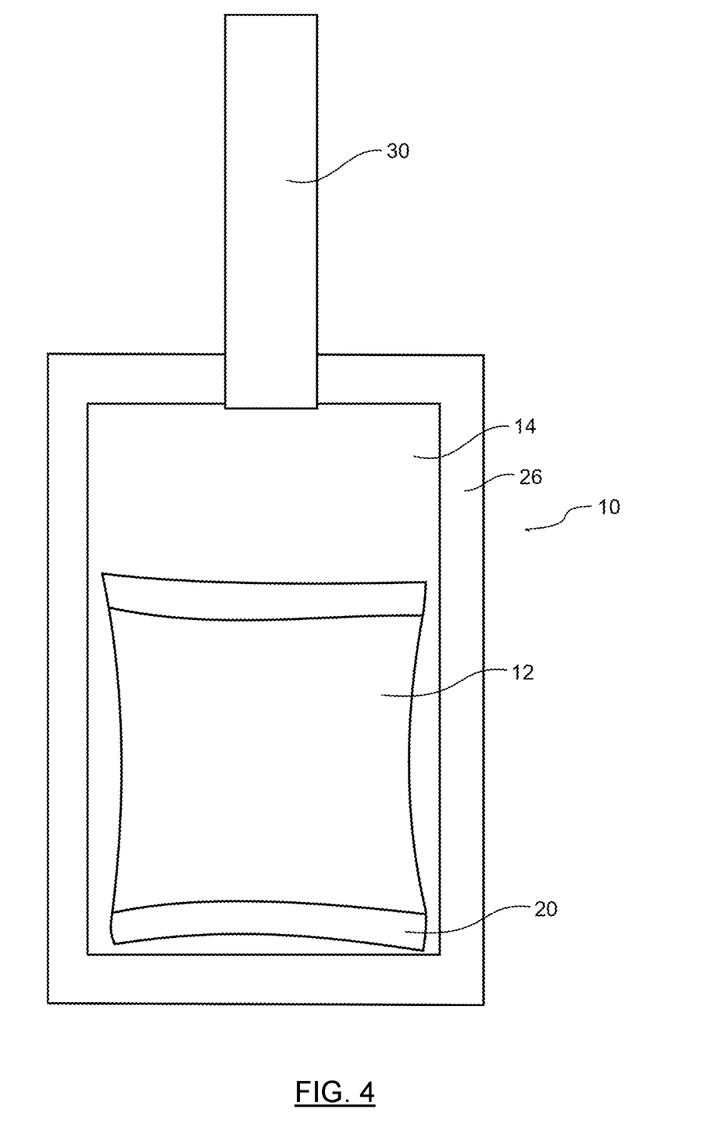
FIG. 4 is a top view of the embodiment of FIG. 1 in the inactivated state additionally showing a securing mechanism.

Referring to FIG. 4, optionally an adhesion strip or other securing mechanism 30 may be affixed to the pack to assist with retaining the pack in contact with a person or object to effect warming.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A heat pack comprising:
    a first sheet and a second sheet bonded together to form a laminated sheet having an interior space;
    a first compartment and a second compartment contained within the interior space;
    a supercooled aqueous salt solution housed in the second compartment, the supercooled aqueous salt solution comprising greater than 15 percent and less than or equal to 25 percent glycerin by mass; and
    a frangible seal between the first and second compartments.

2. The heat pack of claim 1 wherein the supercooled aqueous salt solution is a salt of thiosulphate solution.

3. The heat pack of claim 2 wherein the salt of thiosulphate solution is a sodium thiosulphate solution.

4. The heat pack of claim 1 wherein the supercooled aqueous salt solution is a salt of acetate trihydrate solution.

5. The heat pack of claim 4 wherein the salt of acetate trihydrate solution is a sodium acetate trihydrate solution.

6. The heat pack of claim 1 wherein the supercooled aqueous salt solution has a maximum temperature within a range of 38 to 40 degrees Celsius.

7. The heat pack of claim 1 wherein the supercooled aqueous salt solution has a maximum temperature within a range of 41.7 to 43.3 degrees Celsius.

8. The heat pack of claim 1, wherein the first compartment contains air.

9. The heat pack of claim 1 further comprising a third sheet bonded to one or both of the first and second sheets, wherein the third sheet divides the interior space into the first and second compartments, and wherein the third sheet comprises the frangible seal.

10. The heat pack of claim 1 wherein the first and second sheets are further bonded together to form a seam that divides the interior space into the first and second compartments, and wherein the seam comprises the frangible seal.

11. The heat pack of claim 1 further comprising a third and fourth sheets bonded together to form a laminated sheet having the second compartment;
   wherein the interior space contains the third and fourth sheets; and
   wherein one or both of the third and fourth sheets comprises the frangible seal.

12. The heat pack of claim 1 wherein the supercooled aqueous salt solution comprises 15 to 20 percent glycerin by mass.

13. The heat pack of claim 1 wherein the supercooled aqueous salt solution comprises 19 percent glycerin by mass.

14. The heat pack of claim 1 wherein the supercooled aqueous salt solution comprises 20 to 25 percent glycerin by mass.

15. The heat pack of claim 1 wherein the supercooled aqueous salt solution comprises 22 percent glycerin by mass.

16. A method of warming a heel of an infant for blood sampling, the method comprising applying a heat pack to the infant's heel, the heat pack comprising:
   a first sheet and a second sheet bonded together to form a laminated sheet having an interior space;
   a first compartment and a second compartment contained within the interior space;
   a supercooled aqueous salt solution housed in the second compartment, the supercooled aqueous salt solution comprising greater than 15 percent and less than or equal to 25 percent glycerin by mass; and
   a frangible seal between the first and second compartments.

* * * * *